United States Patent
Deshmukh et al.

(10) Patent No.: US 11,965,413 B2
(45) Date of Patent: Apr. 23, 2024

(54) SYSTEM FOR OPTIMIZATION OF HYDROCARBON PRODUCTION

(71) Applicant: NOV Process & Flow Technologies AS, Fornebu (NO)

(72) Inventors: Salim Deshmukh, Oslo (NO); Geir Vingelven, Høvik (NO); René Mikkelsen, Richmond (GB); Andrea Bassi, Oslo (NO)

(73) Assignee: GRANT PRIDECO, INC., Wilmington, DE (US)

( * ) Notice: Subject to any disclaimer, the term of this patent is extended or adjusted under 35 U.S.C. 154(b) by 312 days.

(21) Appl. No.: 17/420,487

(22) PCT Filed: Jan. 9, 2020

(86) PCT No.: PCT/EP2020/050374
§ 371 (c)(1),
(2) Date: Jul. 2, 2021

(87) PCT Pub. No.: WO2020/144253
PCT Pub. Date: Jul. 16, 2020

(65) Prior Publication Data
US 2022/0098970 A1    Mar. 31, 2022

(30) Foreign Application Priority Data
Jan. 11, 2019   (EP) .................................... 19151530

(51) Int. Cl.
*E21B 27/00*      (2006.01)
*E21B 47/00*      (2012.01)
(Continued)

(52) U.S. Cl.
CPC ........ *E21B 47/006* (2020.05); *E21B 49/0815* (2020.05); *E21B 49/084* (2013.01);
(Continued)

(58) Field of Classification Search
CPC .. E21B 47/006; E21B 49/0815; E21B 49/084; G01N 23/223; G01N 33/2823; G01N 33/2835
See application file for complete search history.

(56) References Cited

U.S. PATENT DOCUMENTS 5,576,974 A * 11/1996 Marrelli ................. G01N 22/04
                                                   702/179
9,689,787 B2    6/2017 Hallset
(Continued)

FOREIGN PATENT DOCUMENTS

WO    2012/053898    4/2012
WO    2018/078609    5/2018

OTHER PUBLICATIONS

Examination Report under Section 18(3) dated Mar. 21, 2022 in corresponding UK Application No. GB2108202.9.
(Continued)

*Primary Examiner* — Benjamin F Fiorello
(74) *Attorney, Agent, or Firm* — Wenderoth, Lind & Ponack, L.L.P.

(57) ABSTRACT

A monitoring system is for a well stream from a hydrocarbon well with seawater injection. The monitoring system includes a sample receiving system, a sample preparation system, an analyzing system, and a pressure control and measurement system. The monitoring system is connectable to a sample point for receiving a sample of the well stream. The sample receiving system includes a fluid conduit connectable for fluid communication with the sample point, and a separator for separating a water fraction from the sample. The sample preparation system includes a filter for filtering the water fraction. The analyzing system includes an x-ray fluorescence analyzer for measurement of a concentration of at least one of dissolved elements Fe, Ba, Ca, S, Cl, P, Cu, Zn, Pb, Br or scale inhibitor tracers in the sample. The
(Continued)

pressure control and measurement system is connected to the sample receiving system or the sample preparation system.

28 Claims, 4 Drawing Sheets

(51) Int. Cl.
*E21B 49/08* (2006.01)
*G01N 23/223* (2006.01)
*G01N 33/28* (2006.01)

(52) U.S. Cl.
CPC ....... *G01N 23/223* (2013.01); *G01N 33/2823* (2013.01); *G01N 33/2835* (2013.01)

(56) References Cited

U.S. PATENT DOCUMENTS

| | | | |
|---|---|---|---|
| 2011/0040501 A1* | 2/2011 | Martin | G01F 1/74 702/45 |
| 2013/0233057 A1* | 9/2013 | Karoum | G01N 21/72 73/31.07 |
| 2014/0124196 A1* | 5/2014 | Sunde | E21B 47/11 166/250.12 |
| 2015/0107824 A1* | 4/2015 | Signorelli | H01G 11/62 166/244.1 |
| 2015/0198038 A1* | 7/2015 | Bartetzko | E21B 41/02 166/250.05 |
| 2016/0131631 A1* | 5/2016 | MacConnell | G01N 33/2835 436/143 |
| 2019/0277729 A1* | 9/2019 | Yan | G01N 33/225 |

OTHER PUBLICATIONS

International Search Report dated Mar. 27, 2021 in International (PCT) Application No. PCT/EP2020/050374.
Extended European Search Report dated Aug. 8, 2019 in European Application No. 19151530.3.
Hobré Analyzer Solutions: "On-line XRF analysis of multiple elements in liquid process streams", C-Quand Brochure 2017, Oct. 9, 2017 (Oct. 9, 2017), pp. 1-6, XP055605589 (Retrieved from the Internet: URL:https://hobre.comjwp-contentjuploads/2017/10/C-QUAND brochure Sep. 10, 2017 2017 pages.pdf [retrieved on Jul. 15, 2019]).
Clement Igwebueze et al., "Calcium Naphthenate Solid Deposit Identification and Control in Offshore Nigerian Fields", Society of Petroleum Engineers, Apr. 8, 2013 (Apr. 8, 2013), pp. 1-13, XP055605544.
C. Yan et al., "Produced Water Analysis by X-Ray Fluorescence with and without the Presence of Crude Oil", Abu Dhabi International Petroleum Exhibition & Conference, Nov. 13, 2017 (Nov. 13, 2017), pp. 1-13, XP055605555, DOI: https://doi.org/10.2118/188225-MS.
Ujile Awajiogak et al., "Evaluating Treatment Process of Produced Water from Oil/Gas Production Platform with Scale Inhibitor", International Journal of Chemical and Process Engineering Research, vol. 1, No. 6, Jan. 1, 2014 (Jan. 1, 2014), pp. 121-131, XP055605560, DOI: 10.18488jjournal.65/2014.1.6/65.6.121.131.
Stephen Heath et al., "SPE-179900-MS The Importance of Scale Inhibitor Analysis in Scale Management—A State of the Art Overview to Provide Cost Effective Scale Control from Simple to Complex Production Scenarios", SPE Oilfield Scale Conference and Exhibition, May 11, 2016 (May 11, 2016), pp. 1-21, XP055605569.

* cited by examiner

SYSTEM FOR OPTIMIZATION OF HYDROCARBON PRODUCTION

BACKGROUND OF THE INVENTION

1. Field of the Invention

The present invention relates to a system and method for optimization of the hydrocarbon production process, particularly the system provides increased knowledge of the origin of the produced water. More particularly a system and method for online scale monitoring. The system and method are particularly applicable for use in monitoring of scale in produced water from hydrocarbon wells and adapting the scale inhibitor usage to the result of the monitoring, preferably in substantially real time.

2. Description of the Related Art

The amount of produced water in a well stream is often referred to as the water cut and is given as a percentage of the well stream. To maintain or increase the well pressure it is well known to use seawater injection wells wherein seawater is injected into the formation to maintain/increase the pressure and thereby force the hydrocarbons out of the formation. The produced water will in such cases be a combination of formation water and injected seawater.

The traditionally measured water cut provides no information on the origin of the water, that is to say, if it is formation water or injected water, or a combination thereof. If it is a combination no information on the size of the different water fractions is available.

Inorganic scale mitigation and prevention programs are of high importance for sustained production in oil and gas fields.

Scaling is the formation of insoluble compounds, such as sulphates and carbonates of barium, calcium, and other ions. Scaling may occur within the formation blocking/narrowing the passages within the formation and thereby reducing the flow from the formation and into the well bore. Scaling may also occur in the production equipment such as pipelines, valves, pumps etc. with a possible negative effect on the function of the equipment.

The most commonly used method of delivering the scale inhibitor solution to the scaling brine has been the "inhibitor squeeze." Here an inhibitor-containing solution is pumped into the water producing zone of the formation, whereby the inhibitor resides on the rock surface. When the wells start producing again, scale inhibitor slowly starts leaching back into the produced-water phase at or above the critical concentration needed to prevent scaling [the minimum inhibitor concentration (MIC), also sometimes referred to minimum effective dose (MED)] in the tubular and near wellbore region. It is intended that the released inhibitor protect the tubulars, as well as the near wellbore. It is expected that the inhibitor adsorb on the formation rock with sufficient capacity to provide "long-term" protection.

Monitoring of the scale inhibitor concentration and the scaling ions in the produced fluid is the key to successful scale management program. As long as the scale inhibitor concentration is above the MIC, scale deposition will not take place in the formation or wellbore. Immediately below the MIC, scale formation may start to occur. Monitoring of suspended solids for their concentration, composition and morphology is also recommended to improve the confidence in gauging the risk of scale formation.

Typical level of MIC is 0.5 to 20 ppm, and at some high temperature high pressure (HTHP) fields that have severe scale problems the MIC can be on the order of a few hundred ppm.

To ensure that the reservoir, tubing and wellbore are protected against scaling, the following three analyses are traditionally performed in order to monitor the effectiveness of and lifetime of the scale squeeze operations.

Considering the low concentrations of the MIC level, high precision of the measurement is required. In order to perform these analyses, sampling and filtration are traditionally performed manually. Subsequently samples are also sent to advanced labs for further analyses. This causes a significant time-lag from when the sample is taken to when an adequate response to concerning changes of the MIC occurs, which means the safety factors of MIC are ramped up, which again means more expensive downtimes executing scale squeeze operations and increased Scale Inhibitor consumption. Especially considering that the majority of the injected scale inhibitor is quickly produced out again when production commences.

Residual Scale Inhibitor concentration (RSI): Produced water is analyzed for scale inhibitor concentration to ensure that there is sufficient (above MIC) scale inhibitor left to inhibit the scale formation in the reservoir, tubing, and wellbore area. A lab derived MIC is used to decide whether system is protected or not.

Produced water ion composition monitoring: Monitoring of the scale forming ions (Ba, Ca, $CaCO_3$, $SO_4$) is performed. A reduction in ion concentration (ex. lower $Ba^{2+}$) compared to expected (based on dilution due to seawater injection) can indicate possible presence of scaling.

Suspended solids monitoring: Produced water is separated from hydrocarbon. Then produced water sample is run through a filtration process. The particles on the filter are analyzed using Scanning Electron Microscope equipped with Energy Dispersive Spectroscopy. This identifies the morphology and composition of the crystals present in the produced water. This confirms if there are any scale particles present and what type ($BaSO_4$, $CaSO_4$, $CaCO_3$) and amount. This is an effective tool to assess the frequency at which a scale squeeze must be repeated in production wells.

WO2018/078609 discloses a method and system for sampling and/or analyzing a production fluid from an oil and gas well. The system is based on providing a large number of reactants for performing the analysis.

U.S. Pat. No. 9,689,787 discloses a system for online monitoring of particle content in an injection water flow.

SUMMARY OF THE INVENTION

The present invention aims at enabling proactive online scale monitoring of produced water from hydrocarbon wells.

A further aim is to provide a system that is applicable for subsea operation.

A further objective is to provide a system for optimizing water injection from one or more injection wells based on monitoring the well stream from the production well.

A further objective is to minimize the manned operation of the production facilities.

The present invention aims at providing a system that enables the online, near real time, monitoring of essential components relevant to prevent scaling of the production system. This is obtained by sampling, preparing, enabling and processing enough volumes to achieve statistically significant and representative measurements, through a high quality XRF having sufficient quality to give reliable results.

This will significantly reduce the time lag from when the sample is taken to when an adequate response to concerning changes of the MIC is available, which means the safety factors of MIC are ramped down, which again means less expensive downtime executing scale squeeze operations and decreased Scale Inhibitor consumption.

The present invention provides a monitoring system for a well stream from at least one hydrocarbon well with seawater injection, wherein the monitoring system is connectable to a well stream sample point for receiving a sample of the well stream, wherein the monitoring system comprises a sample receiving system, a sample preparation system and an analyzing system;
wherein the sample receiving system comprises
a fluid conduit connectable for fluid communication with the well stream sample point and
a separator for separating a water fraction from a well stream sample;
wherein the sample preparation system comprises a filter for filtering the separated water fraction; and
wherein the analyzing system comprises an x-ray fluorescence (XRF) analyzer for measurement of the concentration of at least one of the following dissolved elements Fe, Ba, Ca, S, Cl, P, Cu, Zn, Pb, Br or scale inhibitor tracers in the filtered water sample.

The monitoring system comprises at least one of the following pressure control and measurement systems: a first a pressure control and measurement system connected to the sample receiving system, a second pressure control and measurement system connected to the sample preparation system. These are included to provide for controlled pressure reduction from well pressure to sample measurement pressure.

The need for pressure reduction will depend on the well pressure and pressure window which the analyzers can tolerate. The pressure measurement and control system may be a combination of a pressure sensor and a valve on the gas outlet from the system.

The XRF is pressure sensitive and the system with one or two pressure control systems secures protection of the XRF instrument, especially when the monitoring system is arranged with a fluid connection to a well stream, as the pressure in the well stream may fluctuate.

Further, the sample pressure may influence the composition of the water fraction, as the solution and/or dissolution and/or phase separation of some components is pressure dependent.

The system comprises sample preparation combined with a fast working analysis technique, XRF, which provides an almost instant result. This allows for an adaptive system and close to real time monitoring.

XRF measures the elements dissolved in the water fraction, which corresponds to the dissolved ions in the sample.

The sample preparation system comprises a filter for filtering the separated water fraction and removing particles therefrom before the water sample is analyzed by the XRF. Particles in the sample may result in abrasion of the window of the flow cell of the XRF. Particles may result in scattering and therefore could distort the measurements. However, interesting information about the formation and/or production well is available from XRF analysis of the particles. Therefore, in one embodiment the system comprises conduits and valves to take the retentate stream from the filter, containing particles, bypass the filter and route the sample past the XRF for analysis. After such a measurement thorough flushing to remove the particles will be required.

In one aspect of the system the sample preparation system comprises equipment for further phase separation removing remaining hydrocarbons from the water sample.

In another aspect the sample receiving system comprises a sample receiving vessel having a volume size large enough to receive a statistically significant sample volume to do statistically significant measurements of said dissolved elements, preferably the volume is in the range of 25-500 ml.

In a further aspect the sample preparation system comprises a sample accumulation and circulation tank sized and arranged to receive the filtered sample and to circulate the filtered sample multiple times passed the XRF.

In yet another aspect the XRF analyzer is fluidly connected to at least one calibration liquid tank comprising a liquid with a standard concentration of at least one compound readily identifiable by the XRF for calibration or verification, or both of the XRF measurements. Further this system may comprise a recycle conduit for recycling at least a portion of the analyzed liquid of standard concentration of one compound readily identifiable by the XRF back to the at least one tank. This will reduce the need for calibration liquid.

In another aspect the monitoring system comprises at least one of the following temperature sensors: a first temperature sensor connected to the sample receiving system, a second temperature sensor connected to the sample preparation system.

The temperature of the sample may influence the phase separation and the dissolution of the different components.

In yet another aspect the system comprises a data processor and the XRF analyzer measures the ion concentration of Cl in the sample, and the data processor uses the measurement to calculate the seawater fraction of the produced water in the well stream. To perform the calculation the data processor can use the chloride content of the undiluted formation water and the chloride content of the injection water.

In a further aspect of the system according to the invention the monitoring system is a scale monitoring system, wherein the x-ray fluorescence (XRF) analyzer monitors the concentration of chloride and barium ions in the water fraction. A reduction of the barium concentration in the produced water compared to the expectation based on the chloride concentration is a clear indication that barium is precipitated which means scaling is taking place.

In yet another aspect the analyzing system further comprises a Fourier Transform Infrared Spectroscopy (FTIR) analyzer, or any other suitably applicable measurement instrument, for determining the concentration of scale inhibitor in the filtered water sample.

In one aspect of the system a FTIR analyzer is in a fluid connection with a hydrocarbon fraction separated in the sample receiving system downstream to a separated hydrocarbon outlet to monitor the types and concentration of asphaltenes in the hydrocarbons from the well sample. This solution could also applied in a separate system for monitoring the composition of the hydrocarbon fraction of the well stream, such as wax or asphaltene content.

In yet another aspect the system may comprise a high speed high quality camera or video window exposed to fluid from the sample preparation system, especially a retentate fluid from the filter, such that the camera or video can capture pictures of particles, wherein data from the captured pictures is applicable for calculating the particle type, size and distributions, i.e. applicable for determining the produced water solids concentration, composition and morphology. Solutions for online camera based measuring and monitoring of injection water is for instance known from U.S. Pat. No. 9,689,787B2.

In a further aspect the FTIR analyzer further monitors at least the concentration of one of the following components: mono ethylene glycol (MEG), triethylene glycol (TEG), methanol, kinetic hydrate inhibitors, water, amine, organic acids, or BTEX (benzene, toluene, ethylbenzene and xylenes).

In yet another aspect the system is for monitoring more than one hydrocarbon well and is adapted to selectively receive samples from the hydrocarbon wells, thereby the injection water fraction and/or the scaling of each well may be monitored.

In one aspect of the invention the filter of the sample preparation system restricts particles larger than between 0.1-20 μm from entering the analyzer system.

In a further aspect the sample preparation system comprises a further separator, with an inlet in fluid communication with the separator of the sample receiving system, and an outlet in fluid communication with the filter. The water fraction from the sample receiving system may thereby be undergo further separation in the further separator. This further separator may be operated at a different/lower pressure.

In another aspect of the system the sample preparation system comprises a sample accumulation tank for accumulating the sample. The accumulation tank may function to increase the sample volume and be used to recirculate the accumulated sample passed the XRF and optional FTIR analyzer.

In yet a further aspect of the system the analyzing system comprises a data processor in communication with the analyzer(s) for processing the analysis results determining the seawater fraction. In this aspect of the system the data processor may further be in communication with one or more production well valves and/or seawater injection well valves such that the production of hydrocarbons and/or injection of water is regulated based on the monitoring.

In another aspect the sample receiving system further comprises at least one pH-sensor. The pH of the water fraction influences the dissolution and may also provide information on the carbon oxide concentration.

In a further aspect of the system the monitoring system is part of a remotely operated vehicle (ROV) that is remotely operated fluidly connectable to the well stream sample point. The ROV can be selectively connected to different well stream sample points, thereby monitoring different well at different locations.

The present invention further provides a method for monitoring the well stream from a hydrocarbon well, wherein the method comprises
  passing a sample of the well stream to a sample receiving system
  reducing the pressure of the sample,
  separating a water fraction from the sample,
  filtering the separated water fraction and
  passing the filtered water fraction through a flow cell with a x-ray fluorescence (XRF) analyzer connected thereto, thereby measuring the concentration of at least one ion in the sample.

A person skilled in the art will appreciate that the method is not limited to the listed sequence of the method steps, especially the reduction of the pressure may be performed before and/or after separation of the water fraction.

In one aspect of the method the XRF analyses the content of chloride and the method comprises calculating the seawater fraction in the well stream. In this aspect of the method the results of the monitoring may form the part of the basis for adjusting injection of water in a water injection well.

In a further aspect the XRF analyses the content of chloride and barium ions and the method comprises calculating if the concentration of barium ions is reduced due to scaling, and wherein the method further comprises determining the need for initiating a scale inhibitor squeeze based on the results of the monitoring.

In yet another aspect the method further comprises passing the filtered water sample trough a flow cell with a Fourier Transform Infrared Spectroscopy (FTIR) analyzer for measuring the concentration of dissolved scale inhibitor in the water sample.

In a further aspect the method comprises accumulating the filtered sample in a sample accumulation and circulation tank and circulating the filtered sample multiple (2-200) times passed the XRF, or so that it is passed by the XRF for 1-60 minutes.

In yet another aspect the method comprises calibrating or verification of the XRF analyzer by passing a liquid with a standard concentration of one compound readily identifiable by the XRF is through the XRF flow cell. In this aspect the method may comprise recycling at least a portion of the analyzed liquid of standard concentration of one compound readily identifiable by the XRF from the flow cell back to at least one calibration liquid tank.

The invention aims at providing:
  Availability of real time high quality data on the water fraction of the well stream
  Produced water ionic composition, particularly Ba, Ca, $SO_4$, Cl, P.
  Produced water scale inhibitor concentration
  Produced water solids concentration, composition and morphology
  Data analytics capability based on the availability of rich historical data
  Predictive and proactive scale squeeze management or scale management in general
  Optimized frequency of scale squeeze operation
  Optimized concentration of scale inhibitor

BRIEF DESCRIPTION OF THE DRAWINGS

The enclosed figures are schematic illustrations of the invention or parts thereof. The figures are prepared with the intention to illustrate the connections between the different units. The figures are not drawn up to illustrate the size or exact position of the different equipment.

DETAILED DESCRIPTION OF THE INVENTION

The present invention will now be discussed in further detail with reference to the enclosed figures showing an embodiment thereof. A person skilled in the art will appreciate that some illustrated features are optional and that although only one embodiment is illustrated the invention is not limited to this specific embodiment.

To establish knowledge of the composition of the formation water baseline measurements are performed before the injection water reaches the production well. These measurements include measuring formation particle content and ion content of the formation water.

Figure 1:
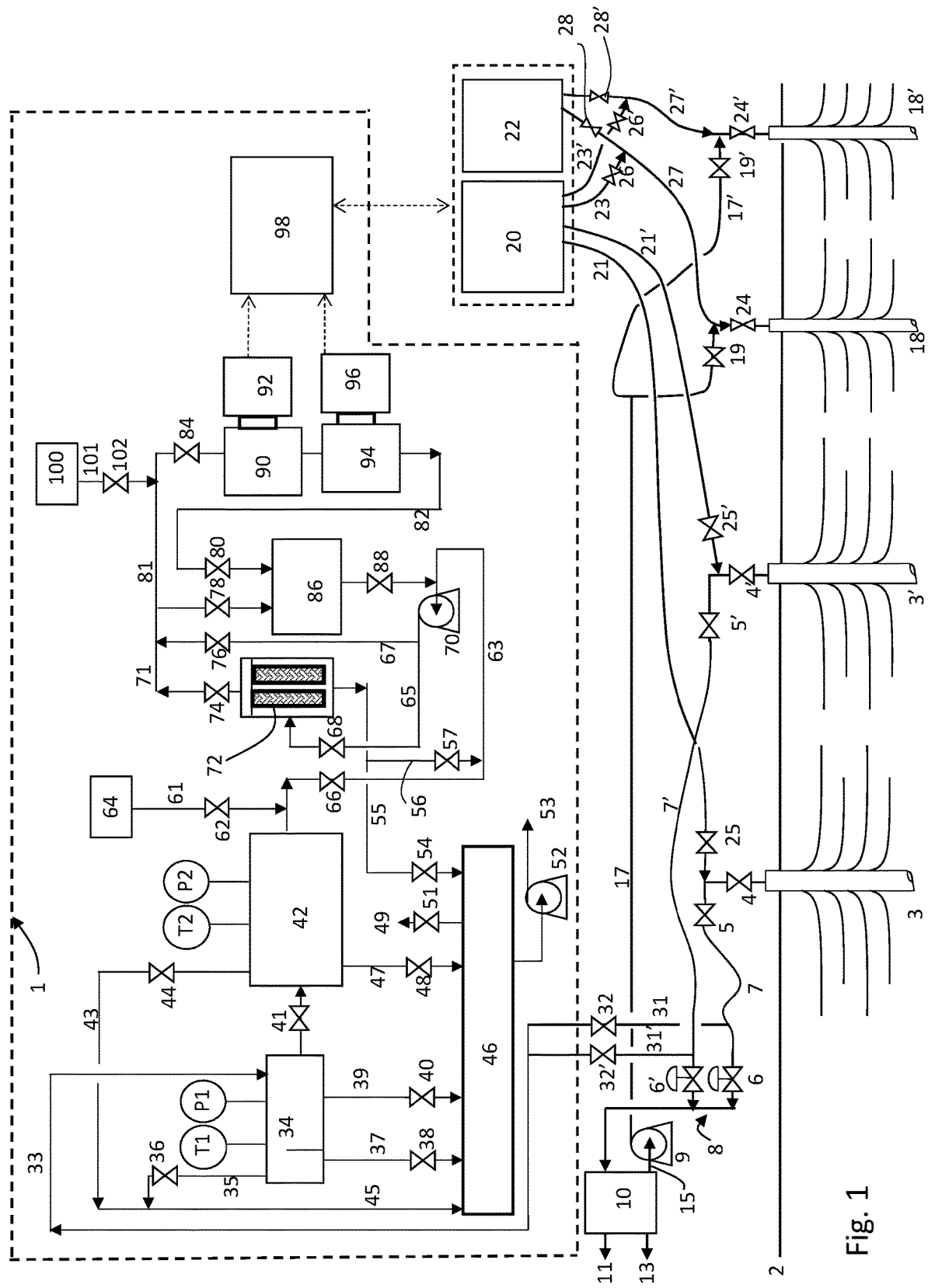
FIG. 1 is an overview of subsea hydrocarbon wells and a system according to the present invention.
Figure 2:
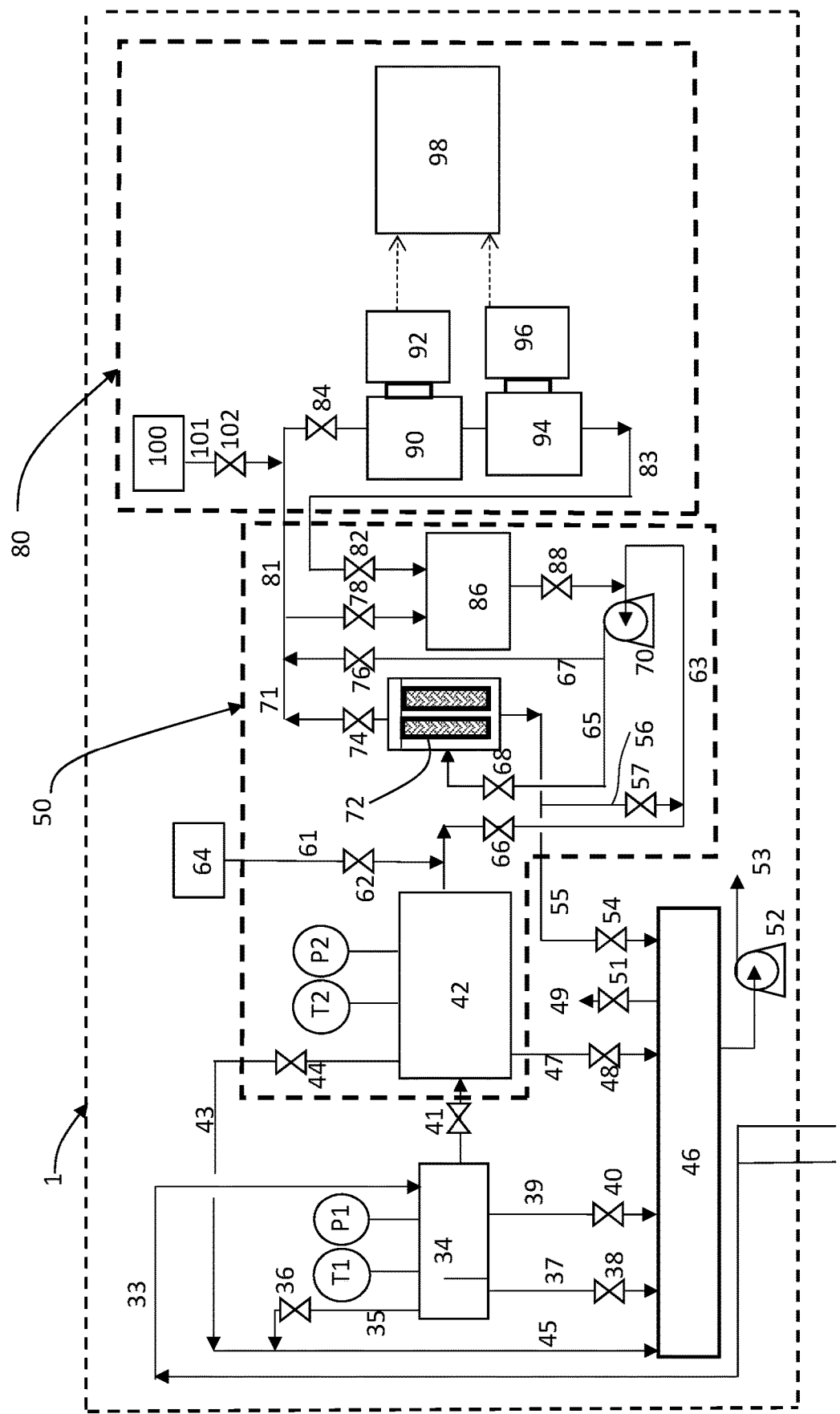
FIG. 2 is an overview of the monitoring system.

FIGS. 1 and 2 illustrate an embodiment of the system.

FIG. 1 shows the seabed 2 with two production wells 3, 3' with production valves 4, 4' and two water injection wells 18, 18' with valves 24,24'. From the production wells the well stream is during production past through valve 4,4' and squeeze valve 5, 5' through well stream conduit 7, 7'respectively to the manifold 8 with valves 6, 6'. From there the combined well stream is passed to a separator 10 providing a gas stream 11 and/or a liquid hydrocarbon stream 13 and produced water 15. Prior to entering the manifold 8 well stream sample point 31, 31' are connected to the respective well stream 7, 7' for withdrawing samples therefrom.

The separator 10 separates the well stream in a gas stream 11, an initial liquid hydrocarbon stream 13 and a produced water stream 15. The produced water may be reinjected, and the water outlet of the separator 10 is connected via pump 9 and conduit 17 with the injection wells. The separator 10 and pump 9 may be arranged topside or subsea. The ion content of the produced water for reinjection is known from the Online Scale Monitoring System, OSM 1.

In the illustrated embodiment the produced water 15 is used for reinjection. Via produced water pump 9 and conduit 17, 17' and valves 19, 19' it can be reinjected. Preferably, flowmeters are connected close to the valves 19,19' measuring the amount of produced water being reinjected. This information is supplied to the data processor and controller 50. The salt content and scale inhibitor content of the reinjected produced water is known from the monitoring system. From seawater treatment unit 22 seawater is provided via valves 28, 28' and conduits 27, 27'. Seawater treatment units are well known and may include sulfur removal units and different filtering such as RO. The seawater treatment unit 22 further comprises equipment for measuring, estimating, calculating the content of $SO_4^{2-}$ and other ions.

From the scale inhibitor tank 20 scale inhibitor may be added to the injection water via pipelines 23, 23' and valves 26, 26'. The scale inhibitor conduits 21, 21' and valves 25, 25 are used for squeezing. During squeezing the production is stopped and valves 5, 5' closed before the scale inhibitor is injected.

The key components of the Proactive/Adaptive OSM system 1 are given below:

1) Three Phase Sample Tapping at High Temperature and Pressure

Tapping at individual wells but the sample is sent to one or multiple sample receiving/preconditioning vessel 34 via valves 32, 32' and well stream sample pipeline 33.

2) Sample Receiving System

Pressure let down to 1 to 5 bars in the system, this can be done in two stages first reduction in the sample receiving system and optionally a second pressure adjustment in the sample preparation system. The system includes level control and separate gas outlet 35 to ease the control of the pressure reduction. The gas can, as illustrated, via gas valve 36, be passed into waste collection tank 46. T1 and P1 are temperature and pressure sensors for controlling the depressurization process.

The method preferably includes using the high-pressure samples from the sampling point to rinse the content of the system with the fresh sample for a duration equivalent to the through flow of at least 3 times the liquid volume in this vessel. This will make sure that new representative sample is collected for further analyses. A typical normal sample size is 25 ml, but to achieve statistical significant measurement the total sampling volume can be multiple times this sample size volume. In one embodiment of the invention the total sampling volume is larger than 2 times the typical normal sample size, in another embodiment sampling volume is 1.01-20 times the typical normal sample size, in another embodiment the total sampling volume is larger than 1.1 times the normal sample size. During this rinsing process the whole sample can be passed on to the top side or closed drain as appropriate.

Once the sample volume is collected, the sample is degassed and while degassing, routing the gas to topside process, which is preferably at a pressure lower than the pressure in the sample receiving vessel or to waste tank as illustrated.

Sample receiving system 34 may include pressure reduction and phase separation equipment, such as gravity separator, a cyclone, an Induced Gas Flotation. The system 34 is equipped with level control and a temperature sensor T1 and pressure sensor P1. The information on the pressure and temperature is transferred to the data processor 98, the data transfer lines are omitted on the figure for clarity reasons.

After degassing, a residence time in the separator (5 to 30 min) to have hydrocarbon (HC)-water separation is allowed.

This separator/vessel 34 is preferably equipped with a interface level measurement instrument. After HC-water separation, a water sample is pumped from this separator 34 via valve 41 to the sample pre-conditioning/preparation system 50 located close to the XRF and FTIR analyzer. Tapping of the sample is below the HC-water interface and approximately halfway into the water phase. This will minimize any settled solids being transferred to the sample pre-conditioning system 50.

The separator 34 is equipped with waste outlets connected via valves 38 and 40 with the waste collection tank 46. The different streams are collected in the waste collection tank 46 equipped with level control. Liquid can be removed from the waste tank 46 via pump 52 as stream 53. Gas is vented from the waste tank 46 as stream 49 via valve 51.

3) Sample Pre-Conditioning/Preparation System 50

This system in one embodiment consists of
- a pre-conditioning vessel 42 to collect the sample from sample receiver vessel/separator 34,
- a preferably regenerable filter 72 to remove any solids larger than 20 μm, preferably lager than 10 μm, more preferably larger than 1 μm, or larger than 0.1 μm, present in the water sample,
- vessel(s) for chemical cleaning reagents (CIP) 64 connected to the outlet stream from vessel 42 via line 61 and valve 62.

In the illustrated embodiment all waste streams are collected in one vessel 46 and pumped from there via pump 52 and line 53 to further handling.

A sample accumulation tank 86.

The system provides for using fresh high-pressure samples from the sample receiving vessel to rinse the content of the sample preconditioning vessel 42, for a duration equivalent to a flow of at least 3 times the liquid volume in this vessel. This will make sure that new representative sample is pumped for analysis. During this rinsing process the whole sample can be passed on to a waste collection vessel 46 or to a closed drain as appropriate.

In one embodiment the system allows for further separation of the HC-water phases in the sample preconditioning vessel 42 with a residence time of 5 to 30 min. the vessel 42 has an outlet 47 connected to the waste collection tank via valve 48. T2 and P2 are temperature and pressure sensors respectively for controlling the process.

This sample preconditioning vessel 42 is preferably also equipped with an interface level measurement instrument. After HC-water separation, the water sample is pumped from this vessel 42 via valve 66, sample conduit 63, sample pump 70 conduit 65, valve 68, filter 72 valve 74, and conduits 71, 81 to the flow cells 90 and 94 located at the XRF and optionally FTIR analyzers respectively. Tapping of the sample is below the HC-water interface and approximately halfway into the water phase, this will minimize any settled solids being transferred to the flow cell.

The collected/removed solid particles are sent to the waste tank 46 via retentate conduit 55 and retentate valve 54.

This system will advantageously have at least one tank 64 for a scale removal/cleaning reagent; organic acids for carbonate scale removal and chelating agents like EDTA for sulphate scale removal. The bypass conduit 67 may be used for the cleaning circuit. By opening valve 76 and closing valves 68, and 78. If necessary, after having filed the analysis system 80 with cleaning fluid valve 66 and 54 may also be closed allowing the cleaning fluid to circulate. Opening valves 66 and 54 again the filter 72 will be backwashed with the cleaning fluid.

Upon scaling or fouling of the flow cell window or the FTIR probe, cleaning reagents can be circulated in a closed loop to clean the flow cell window and tip of the FTIR probe. Spent cleaning agents can be drained to the waste collection vessel 46. Content of this waste collection vessel 46 can be subsequently pumped by pump 52 to produced water treatment system or closed drain at an appropriate frequency.

The instruments of the XRF 90 and if present the FTIR 94 are separated from the fluid by a window in the respective flow cells. The windows can be made of glass or synthetic diamond, or "glassy carbon material".

The accumulation tank 86 allows for the sample to be analyzed several times as the return line 83 via valve 82 transfers the analyzed sample to the tank 86. From the tank 86 if valve 88 is open the sample is pump and filtered and returned to the flow cells, 90, 94.

4) Online Analysis of the Pre-Conditioned Sample

Online XRF analyzer 92

Enables online, nearly real time analysis of the ionic composition of the produced water Ba, Ca, $SO_4$, Cl, P and other ions can be analyzed Profiling the measured chloride concentration in the produced water sample from individual wells.

Estimating the dilution of the formation water by seawater injection, based on the chloride concentration in the formation, seawater and flow rates of respective streams.

Estimate concentration of Ba, Ca, $SO_4$ that corresponds to the dilution of the formation water with seawater and compare it with the actual measured concentration in the produced water.

When measured concentration of the Ba, Ca, $SO_4$ in the produced water per well is lower than what corresponds to dilution, this gives an indication that precipitation/scaling has happened for sulphate-based compounds.

Analysis of the solid samples collected in the sample pre-conditioning filter 72 can be triggered and performed by XRF analyzer 92.

FTIR based spectrophotometry

Enables near real time analysis of the produced water for scale inhibitor, especially organo-phosphonates, BTEX (benzene, toluene, ethylbenzene and xylenes) etc.

The flow cell 90 of the XRF analyzer 92 is fluidly connected to at least one calibration liquid tank 100 via calibration liquid conduit 101 and calibration liquid valve 102. The calibration liquid tank 100 comprises a liquid with a standard concentration of at least one compound readily identifiable by the XRF for calibration or verification, or both of the XRF measurements. In one embodiment the system may be adapted to recirculate at least part of the calibration liquid to the calibration liquid tank after a calibration. A separate return line (not shown) may be included for this purpose.

Additionally, it is also possible to install/employ two monitoring systems in parallel, providing for calibration/verification by comparing the analysis results from the two systems.

Disclosed on FIGS. 1 and 2 are also the possibility to analyze the particles from the formation. The filter 72 is under element analyses by the XRF 92 used to avoid particles in the flow cell 90. In this special operation mode the valves 66, 74 and 54 are closed and valve 57 and 76 are opened. The retentate stream 55 with collected particles from the filter 72 is passed via conduit 56 and the valve 57, pump 70 and filter bypass conduit 67 and inlet line 81 into the flow cell 90. Here the XRF is used to analyze the particles. After such a special operation the system is flushed to remove particles from the analyzing system 80.

5) Online Scale Prediction and Monitoring Tool

The data processor 98 receives the analysis data, but also information on the baseline concentrations and flow-rates of the system.

Software enabling use of real time date from the XRF and FTIR analyzer for predicting and monitoring the scale potential of the produced water for carbonate and sulphate scale.

6) Digital Tool

The digital tool included in or connected to the data processor 98 provides:

Visibility and availability of real time high quality data

Produced water ionic composition—Ba, Ca, $SO_4$, Cl, P

Online monitoring of produced water chloride concentration to enable real time information about the dilution of the formation water chloride by seawater.

Prediction of the dilution of the divalent ions (Ba, Ca, $SO_4$) information that correspond to diluted chloride ions.

Displaying any deviation in the measured divalent ions in produced water from the values that correspond to dilution. Reduction in the divalent ion concentration compared to dilution will indicate possible scale ($BaSO_4$, $CaSO_4$) formation. This could trigger filtering of the sample and characterization of the solids to ascertain the presence of (BaSO$_4$, CaSO$_4$) in the solids.

Produced water scale inhibitor concentration

Data analytics capability based on the availability of rich historical data

Predictive and proactive scale squeeze management

Optimized frequency of scale squeeze operation

Optimized concentration of the scale inhibitor

Figure 3:
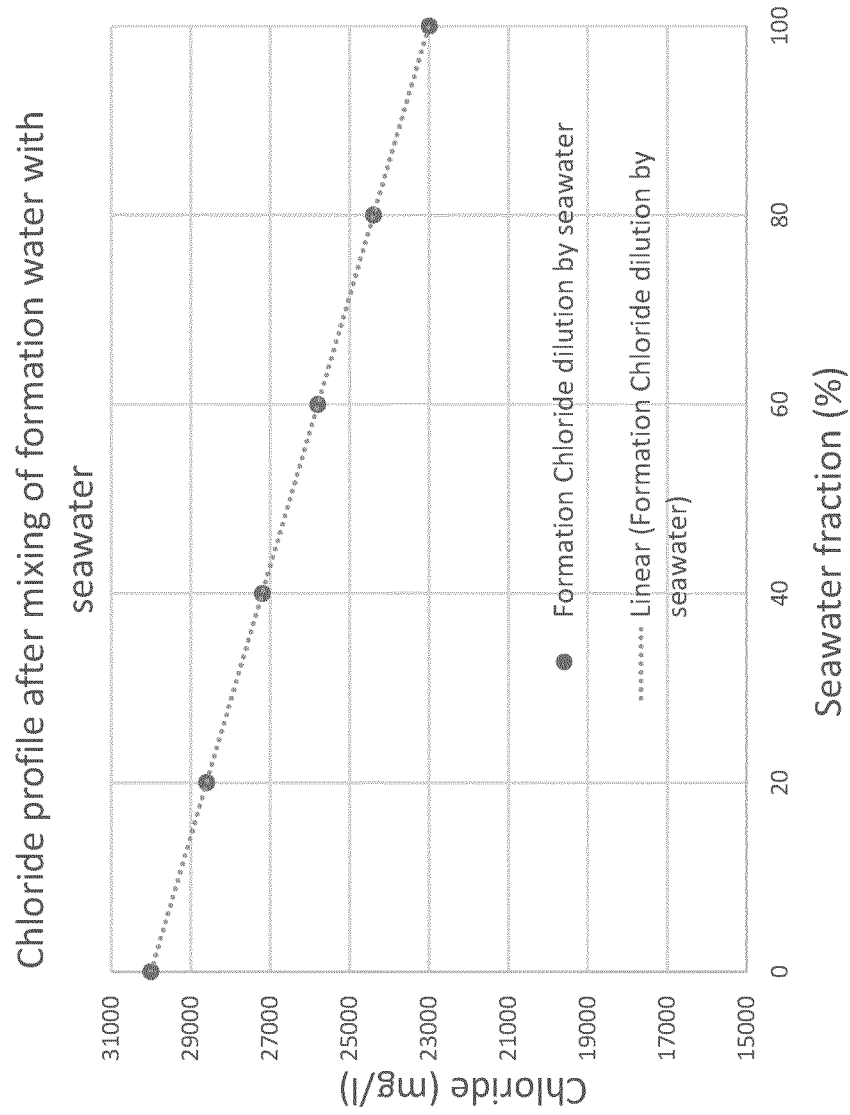
FIG. 3 is a graph showing the chloride content depending on seawater fraction.
Figure 4:
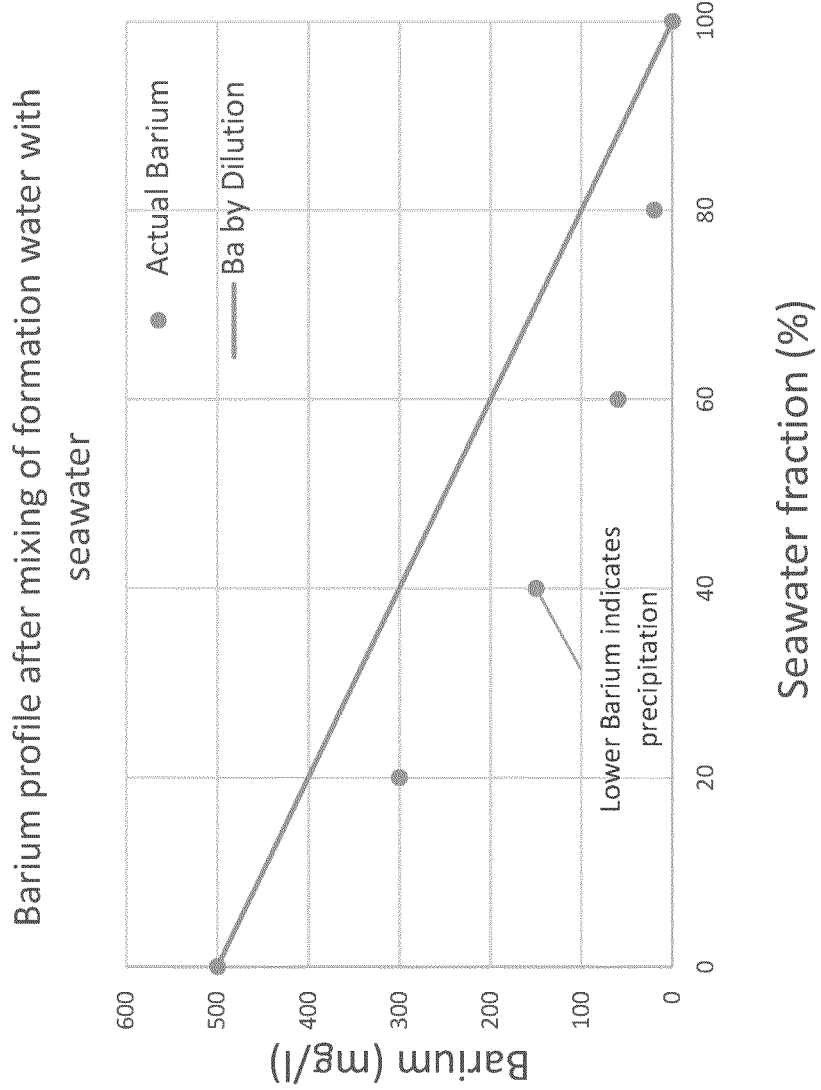
FIG. 4 is a graph showing the barium content as a function of seawater fraction, calculated based on dilution and as measured in case of scaling taking place.

The FIGS. 3 and 4 are provided to illustrate the results that can be obtained. FIG. 3 is an example of a chloride profile in the produced water due to mixing of the formation water from producing wells with injected seawater. The chloride content of the formation water is initially determined as a baseline. The chloride concentration of the injection water is also known and the linear relationship between them allows for the calculation of the line. Thereafter, any measurement of the chloride concentration in the produced water may via the established line be directly translated into the seawater fraction. For instance, if the measured chloride content is 27900 mg/l the seawater fraction is 30%. If the seawater fraction gets very high the well is primarily producing the injected water and of the HC content is going down at the same time the effect of the water injection may no longer be as beneficial.

FIG. 4 illustrates the situation with barium. The graph shows barium ion concentration profile in the produced water due to mixing/dilution of the formation water from producing wells with injected seawater (line) compared to possible actual barium ion concentration in the produced water (circles). Lower actual measured barium ion concentration in the produced water (compared to dilution line) indicates that BaSO$_4$ precipitation has happened. Which means scaling is taking place and a squeeze should be initiate to avoid further scaling.

The system according to the invention allows for optimization of the squeeze operations according to the analysis of the measurements, hence less squeeze operations would be required which results in less downtime of the production, furthermore with better control of scaling risk. Further, if the FTIR analyzer is also included, this will provide additional information on the content of dissolved scale inhibitor in the produced water, providing an independent further indication of when a squeeze is required because the concentration is below the MIC level.

Furthermore, the system according to one preferred embodiment of the invention utilizes the measurements to optimize (minimize both scale risk and scale inhibitor consumption) the combined use of scale inhibitors in water injection at various water injection points, and scale squeeze operation at the various production wells at optimal periods of times during the production life time.

Furthermore, in one embodiment of the invention the ratio between formation water and water injection at the different sample points is measured, which is used to calculate the flow distribution from the water injection from the different water injection points, whereby the flow distribution information can be used to adjust the water injection flow rates at the different water injection points, and the production flow rates at the different wellheads, to optimize the production and minimize the scale risk.

| Reference signs: | |
|---|---|
| 1 | OSM—Online Scale Monitoring System |
| 2 | Seabed |
| 3, 3' | Production well |
| 4, 4' | Production well valve |
| 5, 5' | Squeeze valve |
| 6, 6' | Flow control valve |
| 7, 7' | Well stream |
| 8 | Manifold |
| 9 | Produced water pump |
| 10 | Separator |
| 11 | Gas |
| 13 | Liquid hydrocarbon |
| 15 | Produced water |
| 17 | Reinjection conduit |
| 18, 18' | Water injection well |
| 19, 19' | Reinjection valve |
| 20 | Scale inhibitor tank |
| 21, 21' | Scale inhibitor conduit |
| 22 | Seawater treatment unit |
| 23, 23' | Scale inhibitor pipeline |
| 24, 24' | Injection well valve |
| 25, 25' | Scale inhibitor valve |
| 26, 26' | Scale inhibitor pipeline valve |
| 27, 27' | Seawater injection conduit |
| 28, 28' | Seawater injection valve |
| 31, 31' | Well stream sample point |
| 32, 32' | Well stream sample valve |
| 33 | Well stream sample pipeline |
| 34 | Sample receiving system |
| 35 | Gas outlet |
| 36 | Gas valve |
| 37 | Separated hydrocarbon outlet |
| 38 | Separated hydrocarbon valve |
| 39 | Produced water waste outlet |
| 40 | Produced water waste valve |
| 41 | Sample valve |
| 42 | Sample preparation system |
| 43 | Gas outlet from preparation system |
| 44 | Gas valve on sample preparation system |
| 45 | Waste gas conduit |
| 46 | Waste collection tank |
| 47 | Waste conduit from sample preparation system |
| 48 | Waste conduit valve |
| 49 | Gas waste stream |
| 50 | Sample preparation system |
| 51 | Gas vent valve |
| 52 | Waste pump |
| 53 | Main waste stream |
| 54 | Retentate valve |
| 55 | Retentate stream with solids |
| 56 | Particle sample bypass conduit |
| 57 | Particle sample bypass valve |
| 61 | CIP conduit |
| 62 | CIP valve |
| 63 | Sample conduit |
| 64 | CIP solvent tank |
| 65 | Sample line |
| 66 | Prepared sample valve |
| 67 | Filter bypass conduit |
| 68 | Filter inlet valve |
| 70 | Sample pump |
| 71 | Filtered sample conduit |
| 72 | Filter |
| 74 | Permeate valve |
| 76 | Filter bypass valve |
| 78 | Accumulation tank inlet valve |
| 80 | Flow cell return valve |
| 81 | Sample inlet line |
| 82 | Analysing system |
| 83 | Sample return line |
| 84 | Sample inlet valve |
| 86 | Sample accumulation tank |
| 88 | Accumulation tank outlet valve |
| 90 | XRF flow cell |
| 92 | XRF |
| 94 | FTIR flow cell |
| 96 | FTIR |

| | Reference signs: |
|---|---|
| 98 | Data processor |
| 100 | Calibration liquid tank |
| 101 | Calibration liquid conduit |
| 102 | Calibration liquid valve |

The invention claimed is:

1. A monitoring system for a well stream from a hydrocarbon well with seawater injection, the monitoring system comprising:
    a sample receiving system;
    a sample preparation system;
    an analyzing system; and
    a pressure control and measurement system,
    wherein:
    the monitoring system is connectable to a well stream sample point for receiving a sample of the well stream;
    the sample receiving system comprises: (i) a fluid conduit connectable for fluid communication with the well stream sample point; and (ii) a separator for separating a water fraction from the sample;
    the sample preparation system comprises a filter for filtering the water fraction;
    the analyzing system comprises an x-ray fluorescence analyzer for measurement of a concentration of at least one of dissolved elements Fe, Ba, Ca, S, Cl, P, Cu, Zn, Pb, Br or scale inhibitor tracers in the sample; and
    the pressure control and measurement system is connected to the sample receiving system or the sample preparation system.

2. The monitoring system according to claim 1, wherein the sample receiving system further comprises a sample receiving vessel having a volume size in a range of 25 mL-500 mL.

3. The monitoring system according to claim 1, wherein the sample preparation system further comprises a sample accumulation and circulation tank configured to receive the sample and circulate the sample multiple times past the x-ray fluorescence analyzer.

4. The monitoring system according to claim 1, wherein the x-ray fluorescence analyzer is fluidly connected to a calibration liquid tank configured to receive a calibration liquid with a standard concentration of one compound identifiable by the x-ray fluorescence analyzer for calibration or verification.

5. The monitoring system according to claim 4, further comprising a recycle conduit for recycling at least a portion of the calibration liquid back to the calibration liquid tank.

6. The monitoring system according to claim 1, further comprising a temperature sensor connected to the sample receiving system or the sample preparation system.

7. The monitoring system according to claim 1, further comprising a data processor,
    wherein:
    the x-ray fluorescence analyzer is configured to measure the concentration of Cl in the sample; and
    the data processor is configured to use a measurement from the x-ray fluorescence analyzer to calculate a seawater fraction of produced water in the well stream.

8. The monitoring system according to claim 1, wherein:
    the monitoring system is a scale monitoring system; and
    the x-ray fluorescence analyzer is configured to measure the concentration of Ba and Cl in the sample.

9. The monitoring system according to claim 1, wherein the analyzing system further comprises a Fourier Transform Infrared Spectroscopy analyzer for determining the concentration of the scale inhibitors in the sample.

10. The monitoring system according to claim 9, wherein the Fourier Transform Infrared Spectroscopy analyzer is configured to monitor at least a concentration of: mono ethylene glycol, triethylene glycol, methanol, kinetic hydrate inhibitors, water, amines, organic acids, benzene, toluene, ethylbenzene or xylenes.

11. The monitoring system according to claim 1, wherein the analyzing system further comprises a Fourier Transform Infrared Spectroscopy analyzer in a fluid connection downstream to a separated hydrocarbon outlet for monitoring types and concentrations of asphaltenes in hydrocarbons from the sample.

12. The monitoring system according to claim 1, further comprising a camera or a video window configured to be exposed to a fluid from the sample preparation system such that the camera or the video window can capture pictures of particles, wherein data from the pictures is applicable for calculating a type, size or distribution of the particles.

13. The monitoring system according to claim 1, wherein:
    the hydrocarbon well is one of a plurality of hydrocarbon wells, and the sample is one of a plurality of samples; and
    the monitoring system is configured to selectively receive the plurality of samples from the plurality of hydrocarbon wells.

14. The monitoring system according to claim 1, wherein the filter is configured to restrict particles larger than between 0.1 μm-20 μm from entering the analyzing system.

15. The monitoring system according to claim 1, wherein:
    the separator is a first separator; and
    the sample preparation system further comprises a second separator, with an inlet in fluid communication with the first separator, and an outlet in fluid communication with the filter.

16. The monitoring system according to claim 1, wherein the sample preparation system further comprises a sample accumulation tank for accumulating the sample.

17. The monitoring system according to claim 1, wherein the analyzing system further comprises a data processor in communication with the x-ray fluorescence analyzer for processing analysis results to determine the water fraction.

18. The monitoring system according to claim 17, wherein the data processor is in further communication with one or more production well valves or one or more seawater injection well valves for regulating a production of hydrocarbons or the seawater injection based on monitoring by the monitoring system.

19. The monitoring system according to claim 1, wherein the sample receiving system further comprises a pH-sensor.

20. The monitoring system according to claim 1, wherein the monitoring system is a vehicle configured to be remotely operated and fluidly connectable to the well stream sample point.

21. A method for monitoring a well stream from a hydrocarbon well, the method comprising:
    passing a sample of the well stream to a sample receiving system;
    reducing a pressure of the sample;
    separating a water fraction from the sample,
    filtering the water fraction;
    passing the water fraction through a flow cell, which is fluidly connected to the sample receiving system with an x-ray fluorescence analyzer connected to the flow cell, thereby measuring a concentration of at least one ion in the sample; and calculating a seawater fraction in the well stream, wherein the x-ray fluorescence analyzer analyzes a content of chloride.

22. The method according to claim 21, wherein results of the monitoring form a part of a basis for adjusting injection of water in a water injection well.

23. The method according to claim 21, wherein:

the x-ray fluorescence analyzer analyzes the content of chloride and a content of barium ions; and the method further comprises: (i) calculating if a concentration of the barium ions is reduced due to scaling; and (ii) determining a need for initiating a scale inhibitor squeeze based on results of the monitoring.

24. The method according to claim 21, wherein the flow cell comprises a Fourier Transform Infrared Spectroscopy analyzer for measuring a concentration of a dissolved scale inhibitor in the sample.

25. The method according to claim 21, further comprises:

accumulating the sample in a sample accumulation and circulation tank; and circulating the sample: (i) multiple times past the x-ray fluorescence analyzer; or (ii) such that the sample passes by the x-ray fluorescence analyzer for 1-60 minutes.

26. The method according to claim 25, further comprising recycling a portion of a calibration liquid from the flow cell back to a calibration liquid tank.

27. The method according to claim 21, further comprising calibrating or verifying the x-ray fluorescence analyzer by passing a calibration liquid with a standard concentration of one compound identifiable by the x-ray fluorescence analyzer through the flow cell.

28. The monitoring system according to claim 1, wherein:

the pressure control and measurement system is a first pressure control and measurement system connected to the sample receiving system; and the monitoring system further comprises a second pressure control and measurement system connected to the sample preparation system.

* * * * *